United States Patent
Brod

(10) Patent No.: US 10,581,300 B2
(45) Date of Patent: Mar. 3, 2020

(54) ELECTRIC MOTOR WITH ROTARY ENCODER

(71) Applicant: BÜHLER MOTOR GMBH, Nürnberg (DE)

(72) Inventor: Sabrina Brod, Nürnberg (DE)

(73) Assignee: BÜHLER MOTOR GMBH, Nürnberg (DE)

( * ) Notice: Subject to any disclaimer, the term of this patent is extended or adjusted under 35 U.S.C. 154(b) by 250 days.

(21) Appl. No.: 15/483,051

(22) Filed: Apr. 10, 2017

(65) Prior Publication Data

US 2017/0294824 A1  Oct. 12, 2017

(30) Foreign Application Priority Data

Apr. 11, 2016  (DE) .......................... 10 2016 106 581

(51) Int. Cl.
| | |
|---|---|
| H02K 11/22 | (2016.01) |
| H02K 29/10 | (2006.01) |
| H02K 7/116 | (2006.01) |
| A61M 5/142 | (2006.01) |

(52) U.S. Cl.
CPC ............ H02K 11/22 (2016.01); A61M 5/142 (2013.01); H02K 7/116 (2013.01); H02K 29/10 (2013.01); *A61M 2205/3306* (2013.01)

(58) Field of Classification Search
CPC ........ H02K 11/22; H02K 7/116; H02K 29/10; A61M 5/142; A61M 2205/3306
USPC .................................................. 310/68 B, 83
See application file for complete search history.

(56) References Cited

U.S. PATENT DOCUMENTS

| | | | | |
|---|---|---|---|---|
| 4,169,990 | A | * | 10/1979 | Lerdman ................. F23N 3/082 318/400.29 |
| 4,377,744 | A | * | 3/1983 | Mocenter ................. G02B 7/30 250/231.18 |
| 4,638,433 | A | * | 1/1987 | Schindler .............. E05F 15/668 160/189 |
| 5,224,429 | A | * | 7/1993 | Borgman ................. A47B 9/00 108/147 |
| 5,650,679 | A | * | 7/1997 | Boggs, III ........... H01R 39/646 310/105 |
| 6,072,296 | A | * | 6/2000 | Grieb ................... H02K 7/1025 318/602 |
| 10,099,005 | B2 | * | 10/2018 | Gao ....................... A61M 5/142 |
| 10,122,243 | B2 | * | 11/2018 | Hirai ...................... H02K 5/161 |

(Continued)

FOREIGN PATENT DOCUMENTS

JP         S61231851         * 10/1986

*Primary Examiner* — Jermele M Hollington
*Assistant Examiner* — Ahmed Elnakib
(74) *Attorney, Agent, or Firm* — Westerman, Hattori, Daniels & Adrian, LLP

(57) ABSTRACT

An electric motor with a motor shaft, a motor pinion and a sensor element for an optical rotary encoder which has at least one recess for the transmission of a light beam from the optical rotary encoder. The motor shaft, the motor pinion and the sensing element being integrally formed with one another and being coupled with the motor shaft in a rotationally fixed manner. Further, the sensor element has a drum-shaped design and is aligned coaxially with the motor pinion. The recess is formed in the sensor element in such a way that the light beam of the rotary encoder can pass radially relative to a rotational axis of the sensor element. The invention also relates to a medical device with such an electric motor.

13 Claims, 4 Drawing Sheets

(56) References Cited

U.S. PATENT DOCUMENTS

| | | | |
|---|---|---|---|
| 2005/0168187 A1* | 8/2005 | Uchiyama | G01P 3/486 318/772 |
| 2009/0015111 A1* | 1/2009 | Chen | H02K 11/22 310/68 B |
| 2009/0278486 A1* | 11/2009 | Lin | H02K 11/21 318/466 |
| 2011/0286723 A1* | 11/2011 | Wang | H02P 7/285 388/809 |
| 2014/0312819 A1* | 10/2014 | Murata | H02K 11/22 318/400.38 |
| 2015/0008802 A1* | 1/2015 | Fukuda | G01D 5/3473 310/68 B |
| 2015/0268642 A1* | 9/2015 | Nessel | H02P 8/16 700/282 |
| 2015/0372543 A1* | 12/2015 | Lobo | H02K 1/14 310/46 |
| 2017/0294824 A1* | 10/2017 | Brod | H02K 11/22 |

* cited by examiner

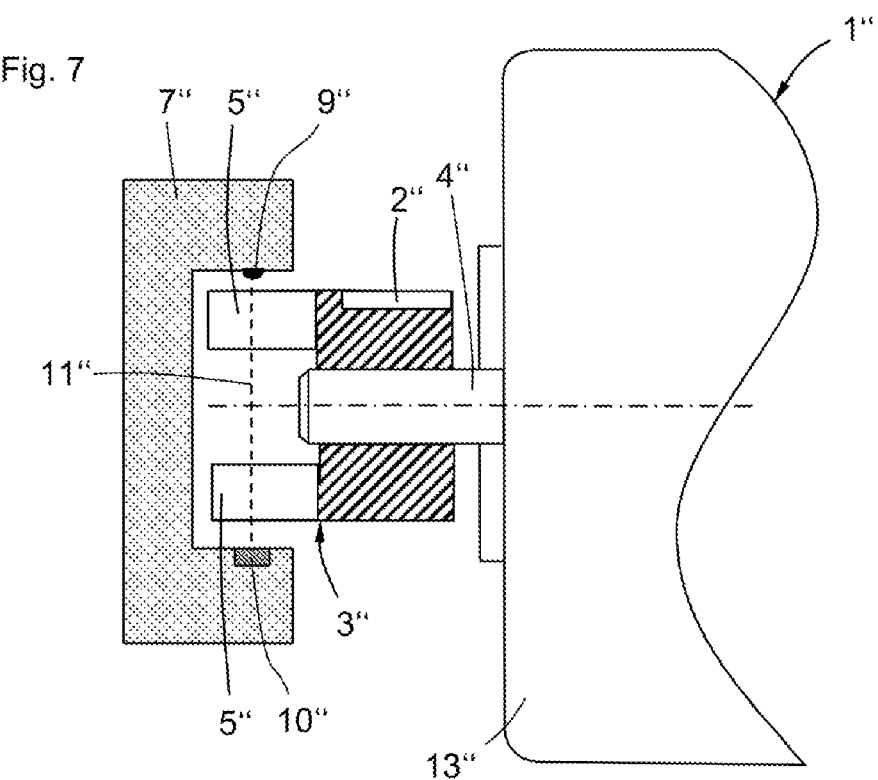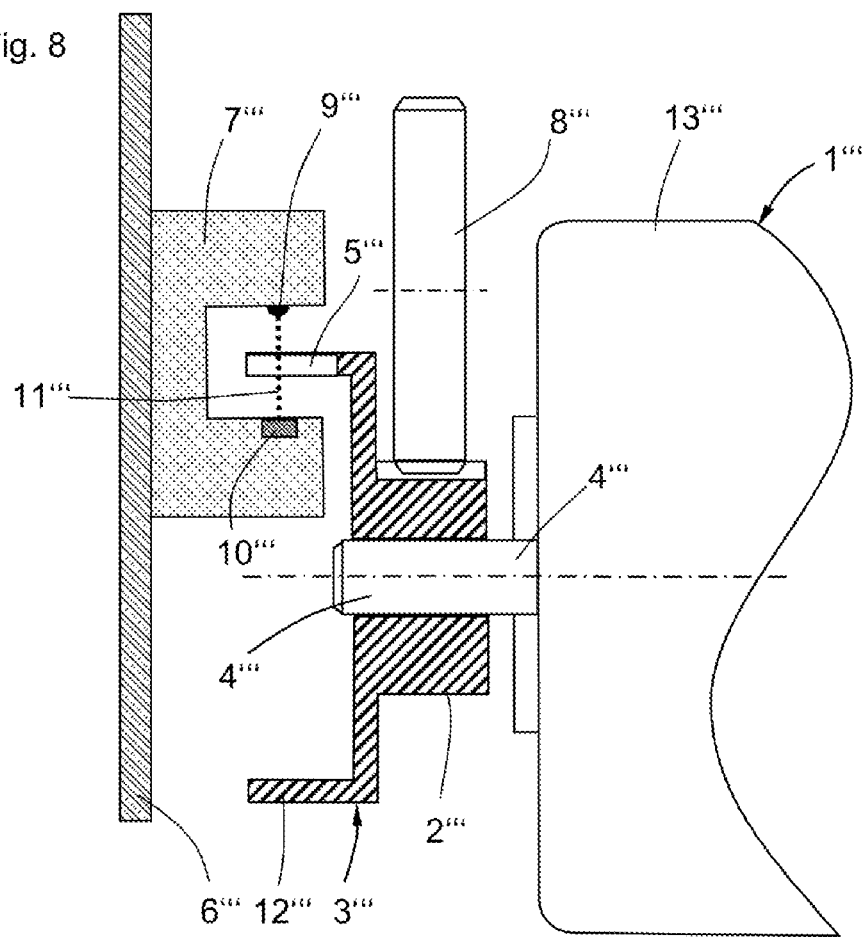

ELECTRIC MOTOR WITH ROTARY ENCODER

BACKGROUND OF THE INVENTION

(1) Field of the Invention

The invention relates to an electric motor with a rotary encoder. The invention also relates to a medical device, in particular a syringe pump or infusion pump, with such an electric motor.

(2) Description of Related Art Including Information Disclosed Under 37 CFR 1.97 and 1.98

An electric motor of the type mentioned in the beginning is known, for example, from US 2015268642 A1. The known electric motor has an electromechanical drive unit, through which a motor shaft extends. The motor shaft protrudes beyond a housing of the electric motor and is firmly connected to a motor pinion. Between the motor pinion and the motor housing, a sensor element is arranged in the form of a disc provided with recesses. The sensor element has a cross-sectional diameter that is greater than the cross-sectional diameter of the motor pinion, and is operatively connected to an optical rotary encoder that is arranged radially outside the sensor element. The rotary encoder forms a light barrier, the light beam of which is temporarily shaded when the sensor element is rotated. The recesses in the sensor element allow for the passage of the light beam.

A disadvantage of the previously known electric motor is the relatively large radial structural space required by the arrangement of the sensor element and the rotary encoder. For example, in medical syringe pumps, small dimensions of the drive unit are required in order to be able to design the syringe pump compactly.

The objective of the invention is to specify an electric motor which has as small a radial construction space as possible and can be produced simply and inexpensively. It is also an objective of the invention to provide a medical device, in particular a syringe pump or infusion pump, with such an electric motor.

BRIEF SUMMARY OF THE INVENTION

The present invention is based on the idea of proposing an electric motor with a motor shaft, a motor pinion and a sensor element for an optical rotary encoder, wherein the sensor element has at least one recess for the transmission of a light beam of the optical rotary encoder. The motor pinion and the sensing element are integrally formed with one another and are coupled with the motor shaft in a rotationally fixed manner. The sensor element has a drum-shaped design and is aligned coaxially with the motor pinion. In this case, the recess in the sensor element is designed such that the light beam of the rotary encoder can pass radially to a rotational axis of the sensor element.

As a result of the drum-shaped design of the sensor element, it is possible to arrange the rotary encoder axially to the motor pinion. This reduces the installation space in the radial direction. The axial arrangement of the rotary encoder is also made possible by the arrangement of the recess which is formed in the sensor element in such a way that the light beam of the rotary encoder can pass radially through the recess. The drum shape of the sensor element is, moreover, easy to produce and thus inexpensive.

Preferably, the motor pinion is arranged between the sensing element and a motor housing. In particular, the invention preferably provides that the sensor element extends longitudinally axially beyond the motor shaft. In other words, the sensor element can be arranged on the end face of the motor pinion. The frontal arrangement of the sensor element makes it possible to arrange the rotary encoder in the longitudinal direction of the motor shaft in order to reduce the radial structural space. The rotary encoder can thereby directly reach the sensor element, so that overall the production of the electric motor is simple and cost-effective. At the same time, the compact arrangement of the electric motor is made possible by the arrangement of the sensor element on the end face.

In the case of the invention, it is preferably provided that the recess in the sensor element is limited by two material segments of the sensor element for shadowing out the light beam of the rotary encoder. The material segments, together with the recess, generally form a sequence of shadowing regions and permeable regions so that, during the rotation of the sensor element, the light beam of the rotary encoder is intermittently interrupted and temporarily transmitted. As a result, a signal, in particular a square-wave signal, is generated in the rotary encoder, the frequency of the light shading and light transmission providing information about the rotational speed of the electric motor.

It is preferably provided that the two material segments extend in parallel to a rotational axis of the sensor element and delimit two recesses. The recesses can be formed, in particular, by a groove extending radially and completely through the sensor element. Such a design of the sensor element is particularly simple to produce. In particular, such a configuration is preferred for small diameters of the sensor element, in which the space is not sufficient for a higher number of recesses. Due to the groove extending radially and completely through the sensor element, two recesses are essentially formed and arranged at an angle of 180 degrees. In any case, the light beam of the rotary encoder can pass completely through the groove, so that the groove allows the light beam to pass twice during a complete revolution of the sensor element. The material segments delimiting the groove shadow the light beam.

In particular, it can be provided that each of the two material segments has a cylindrical segment-shaped outer surface and a flat inner surface. The inner surfaces of the material segments are preferably arranged parallel to one another and delimit the groove. In other words, the inner surfaces of the material segments form the groove side walls. Since the material segments have a full-surface, in particular part-circular, cross-sectional contour, the stability of the material segments is comparatively high, even if the overall cross-sectional diameter of the sensor element is very small. Overall, high stability is ensured even in the case of small structures.

In a preferred embodiment of the electric motor, it is provided that the sensor element is hollow-cylinder-shaped. The material segments can have a uniform wall thickness. In particular, the material segments can delimit at least two, especially at least three, especially at least four, recesses. A higher number of recesses increases the accuracy in determining the rotational speed of the electric motor and the current rotational position of the electric motor. This is preferred in many applications. The arrangement of the rotary encoder is also improved by the hollow cylindrical design of the sensor element. In particular, the inner cylindrical cavity in the sensor element can be used at least to partly allow the rotary encoder to engage the sensor element. This further contributes to the reduction in the radial installation space.

For all embodiments of the invention, the motor pinion and the sensor element are preferably designed as a single, in particular one-piece, injection-molded part. In this case, the motor pinion and the sensing element can be produced as a single plastic injection-molded part or as a metal powder injection-molded part, in particular produced by metal-injection molding. This production method further simplifies serial production of the electric motor and contributes to the reduction of the production costs. Moreover, the use of tools is reduced during manufacture because, during injection molding, the recess in the sensor element can be produced at the same time.

In a preferred variant of the electric motor according to the invention, a rotary encoder with a light source and a light receiver is provided. The sensor element can thus be arranged between the light source and the light receiver in such a way that a direct light beam between the light source and the light receiver can be released by the recess and/or can be shaded by the material segments. The rotary encoder can essentially form a light barrier, which results in high accuracy in the detection of the rotational speed and rotational position of the electric motor. In addition, a light barrier is hardly susceptible to interference, so that high operational safety of the electric motor is ensured.

The light beam of the rotary encoder is preferably aligned radially with respect to the longitudinal axis of the sensor element. The radial alignment of the light beam results from the positioning of the rotary encoder which is aligned axially with respect to the motor shaft, this positioning of the rotary encoder leading to a reduction in the radial installation space of the electric motor.

In a preferred variant, a provision is made for the light source and the light receiver to be arranged radially outside the sensor element opposite to each other. In other words, the rotary encoder is arranged in such a way that the sensor element projects completely between the light source and the light receiver. In particular, the rotary encoder can be aligned coaxially with the sensor element. Such an arrangement of the rotary encoder is particularly simple to implement and increases the ease of maintenance, since the rotary encoder can be easily removed and replaced laterally.

In a further preferred embodiment of the electric motor according to the invention, the light source is arranged radially inside the sensor element and the light receiver radially outside the sensor element. Alternatively, the light receiver can be arranged radially inside the sensor element and the light source can be arranged radially outside the sensor element. The above mentioned arrangement possibilities of the rotary encoder are provided, in particular, when the sensor element is hollow-cylindrical in shape. The rotary encoder can then be arranged such that a light-barrier element, in particular the light source or the light receiver, is arranged outside the sensor element, and within the sensor element and another light-barrier element, in particular the light receiver or the light source. Overall, a particularly compact design of the electric motor can thus be achieved.

Preferably, the light source and the light receiver are mounted on a common sensor circuit board. The sensor circuit board is preferably arranged axially spaced from the sensor element. The use of a common sensor circuit board facilitates the manufacture of the electric motor and leads to a compact design. In particular, in contrast to electric motors known from the prior art, it is avoided that the sensor circuit board is arranged laterally to the electric motor, which would increase the radial structural space.

Due to the axial alignment of the sensor circuit board, the radial installation space is reduced.

In a further preferred embodiment of the electric motor, at least two rotary encoders are provided, each of which forms a light barrier. In this case, the light barriers can be offset by an angle off the longitudinal axis of the sensor element that is not equal to 180 degrees. In particular, the angle can also be other than 90 degrees. The use of at least two rotary encoders leads to advantageous redundancy so that, in the event of a rotary encoder failing, operation of the electric motor is still possible. This is particularly preferred in medical applications. Due to the arrangement of the rotary encoders in such a way that their light barriers are arranged at an acute angle to each other, the recognition accuracy is also significantly improved. In particular, a rotation detection can be made possible by the two rotary sensors, preferably with light barriers arranged at an acute angle to one another. This not only detects the rotational speed and the current rotational position of the electric motor but also the direction, in which the electric motor, in particular the motor shaft, rotates.

The objective of the invention mentioned in the beginning is in particular also solved by a medical device, specifically a syringe pump or an infusion pump, which has a previously described electric motor. Particular preference is given to the use of the electric motor in a syringe pump, wherein the syringe pump can also include a spur gear, which is connected to the motor pinion of the electric motor. The spur gear can be coupled with a threaded spindle which acts on a syringe plunger of a syringe clamped in the syringe pump. In this way, small amounts of a medication can be continuously administered or infused over a prolonged period with high accuracy.

BRIEF DESCRIPTION OF THE SEVERAL VIEWS OF THE DRAWINGS

The invention is better understood by reading the following Detailed Description of the Preferred Embodiments with reference to the accompanying drawing figures, in which like reference numerals refer to like elements throughout, and in which:

FIG. 7 shows a cross-sectional view through a part of an electric motor according to a third preferred embodiment, the sensor element completely projecting into a rotary encoder; and FIG. 8 shows a cross-sectional view of a part of an electric motor according to a further preferred embodiment with an alternative design of the motor pinion and sensor element.

The attached drawings show a total of four different embodiments of the invention. The symbols referring to the individual exemplary embodiments have a different number of prime marks in them. FIGS. 1 to 3 show a first exemplary embodiment, FIGS. 4 to 6 show a second exemplary embodiment, FIG. 7 shows a third exemplary embodiment, and FIG. 8 shows a fourth exemplary embodiment.

DETAILED DESCRIPTION OF THE INVENTION

Figure 1:
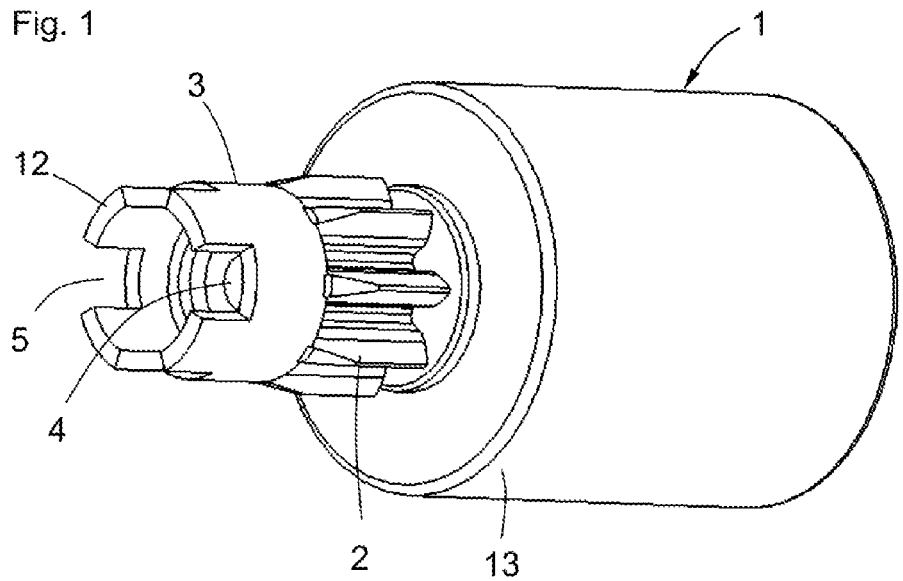
FIG. 1 shows a perspective view of an electric motor according to the invention and to a first preferred embodiment.

In describing preferred embodiments of the present invention illustrated in the drawings, specific terminology is employed for the sake of clarity. However, the invention is not intended to be limited to the specific terminology so selected, and it is to be understood that each specific element includes all technical equivalents that operate in a similar manner to accomplish a similar purpose.

An electric motor 1, which has a motor housing 13, is common to all exemplary embodiments. A motor shaft 4, on which a motor pinion 2 is seated, projects axially from the motor housing. The motor pinion 2 is integrally connected to a sensor element 3, the sensor element 3 being of a drum-shaped design. In particular, the sensor element 3 has a cylindrical outer peripheral surface. In all exemplary embodiments, the sensor element 3 is aligned coaxially with the motor pinion 2. In particular, the motor pinion and the sensing element are integrally formed with one another, preferably as a single injection-molded part.

The sensor element has at least one recess 5, which forms a passage for a light beam 11 of a rotary encoder 7 (See FIGS. 7 and 8 for schematic representations of a light beam arrangement found in all embodiments of a rotary encoder). In the first exemplary embodiment, it can be clearly seen in FIG. 1 that the sensor element 3 is essentially hollow-cylindrical. In particular, the sensor element 3 has material segments 12, which in each case delimit recesses 5. The material segments 12 are curved. Specifically, the material segments 12 follow the hollow cylinder shape of the sensor element 3. The material segments 12 have a uniform wall thickness.

The motor pinion 2, which is connected in a rotationally fixed manner to the motor shaft 4, integrally adjoins the sensor element 3. The motor shaft 4 preferably terminates in the region of a bottom surface of the sensor element 3. In particular, the sensor element 3 extends longitudinally beyond the motor shaft 4. In this respect, the motor pinion 2 is arranged between the sensor element 3 and the motor housing 13.

In the case of the first exemplary embodiment, the sensor element 3 has four recesses, which are each offset at an angle of 90 degrees to each other. The recesses 5 have a uniform width. Furthermore, the recesses 5 are uniformly spaced from each other. In other words, the material segments 2 also have a uniform width. In this way, the recesses 5 are arranged such that in each case two recesses 5 are arranged radially opposite one another. Radiality refers to the longitudinal axis of the motor shaft 4, i.e., the rotational axis of the electric motor 1.

Figure 2:
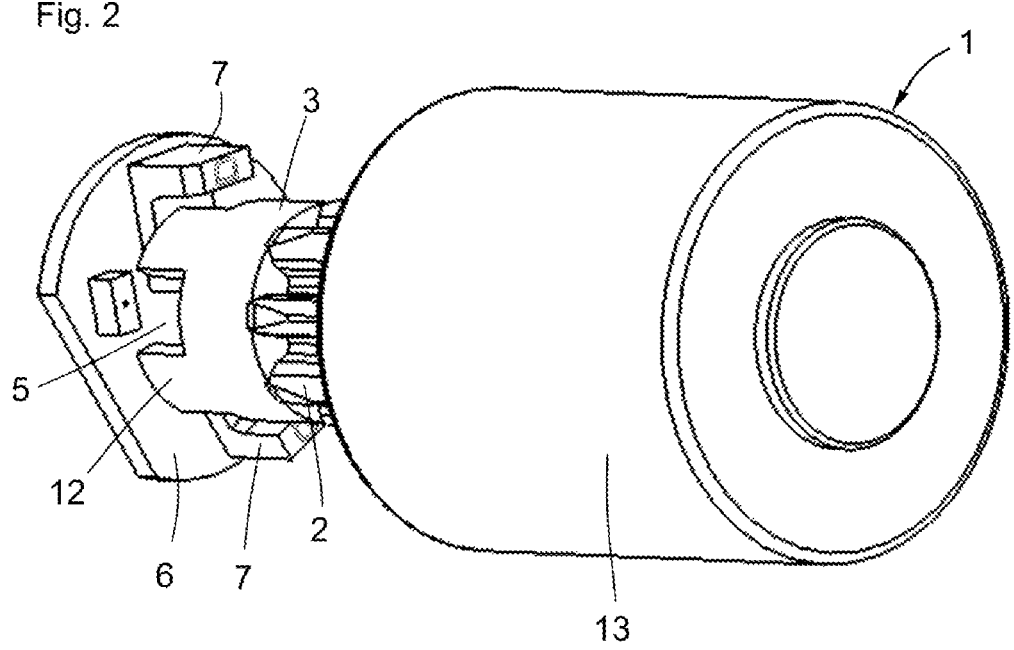
FIG. 2 is a perspective view of the electric motor according to FIG. 1 with a rotary encoder.

As can be clearly seen in FIG. 2, the electric motor 1 also has an encoder with a sensor circuit board 6, two rotary encoders 7 being arranged on the sensor circuit board 6. The rotary encoders 7 each form a light barrier. For this purpose, each rotary encoder 7 has a light source 9 and a light receiver 10 (See FIGS. 7 and 8 for a schematic representation of light source 9 and light receiver 10 found in all examples of the rotary encoders 7). A light beam 11 can be activated between the light source 9 and the light receiver 10 and be temporarily interrupted by the sensor element 3 when the electric motor 1 is rotated. In particular, the material segments 12 provide for an interruption of the light beam 11, whereas the recesses 5 allow the light beam 11 to pass.

In the first exemplary embodiment, it is provided that the rotary encoders 7 are arranged such that in each case a light-barrier element, respectively the light source 9 or the light receiver 10, engages with the sensor element 3. In particular, a light-emitting element is arranged radially inside the sensor element 3, whereas a different light-receiving element is arranged radially outside the sensor element 3. Both rotary encoders 7 are arranged on the common sensor circuit board 6, which is positioned axially spaced from the sensor element 3. The sensor circuit board 6 is essentially coaxial with the motor housing 3.

Figure 3:
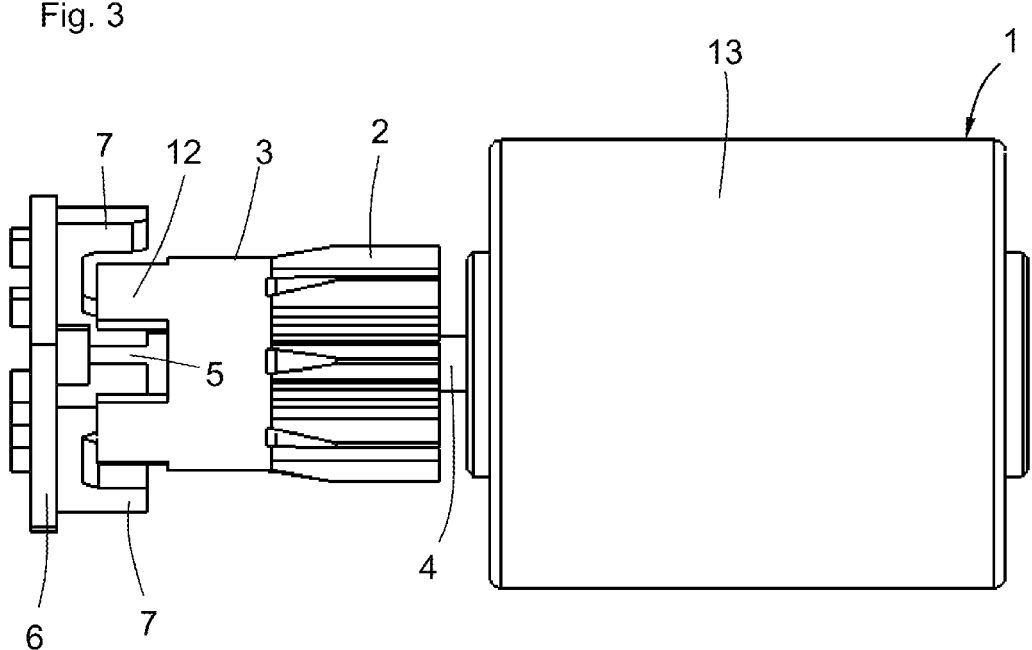
FIG. 3 is a side view of the electric motor according to FIG. 2.

The arrangement of the rotary encoders 7 with respect to the sensor element 3 is clearly shown in FIG. 3. It can also be seen that, in the first exemplary embodiment, the sensor element 3 has a cross-sectional diameter that is smaller than the cross-sectional diameter of the motor pinion 2. Thus, a particularly compact construction is achieved, in particular with regard to the radial structural space.

FIG. 2 also clearly shows that the two light barriers, which are formed by the two rotary encoders 7, are aligned at an angle to one another. The light barriers are thus positioned in such a way that their light beams 11 assume an angle which is not equal to 180 degrees or to 90 degrees. In this respect, the light barriers are arranged at an acute angle to one another. Thereby, rotational direction detection can be implemented.

Figure 4:
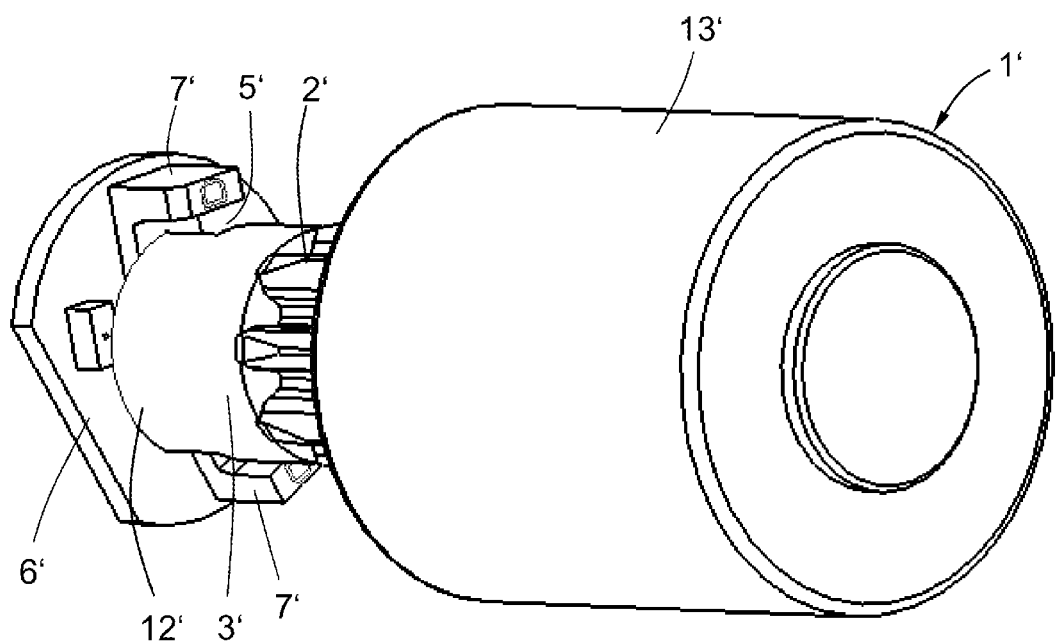
FIG. 4 shows a perspective view of an electric motor with a rotary encoder according to a second preferred exemplary embodiment with an alternative configuration of the sensor element.
Figure 5:
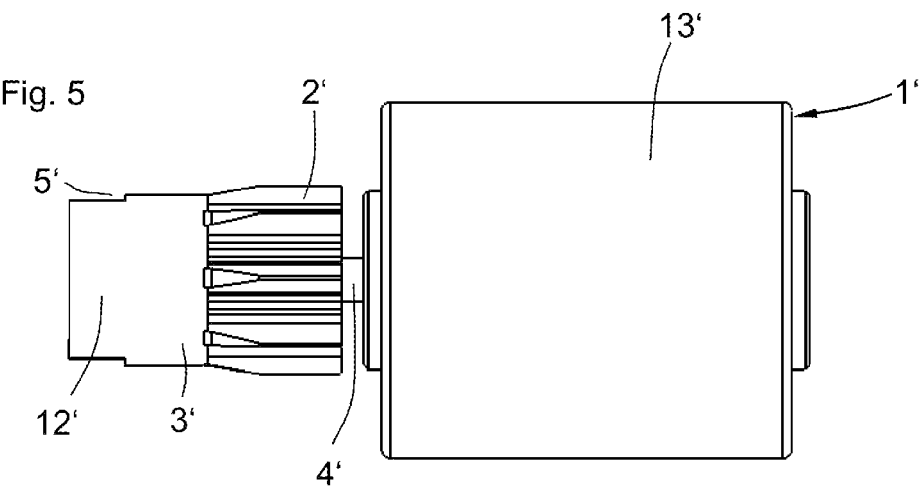
FIG. 5 is a side view of the electric motor according to FIG. 4.
Figure 6:
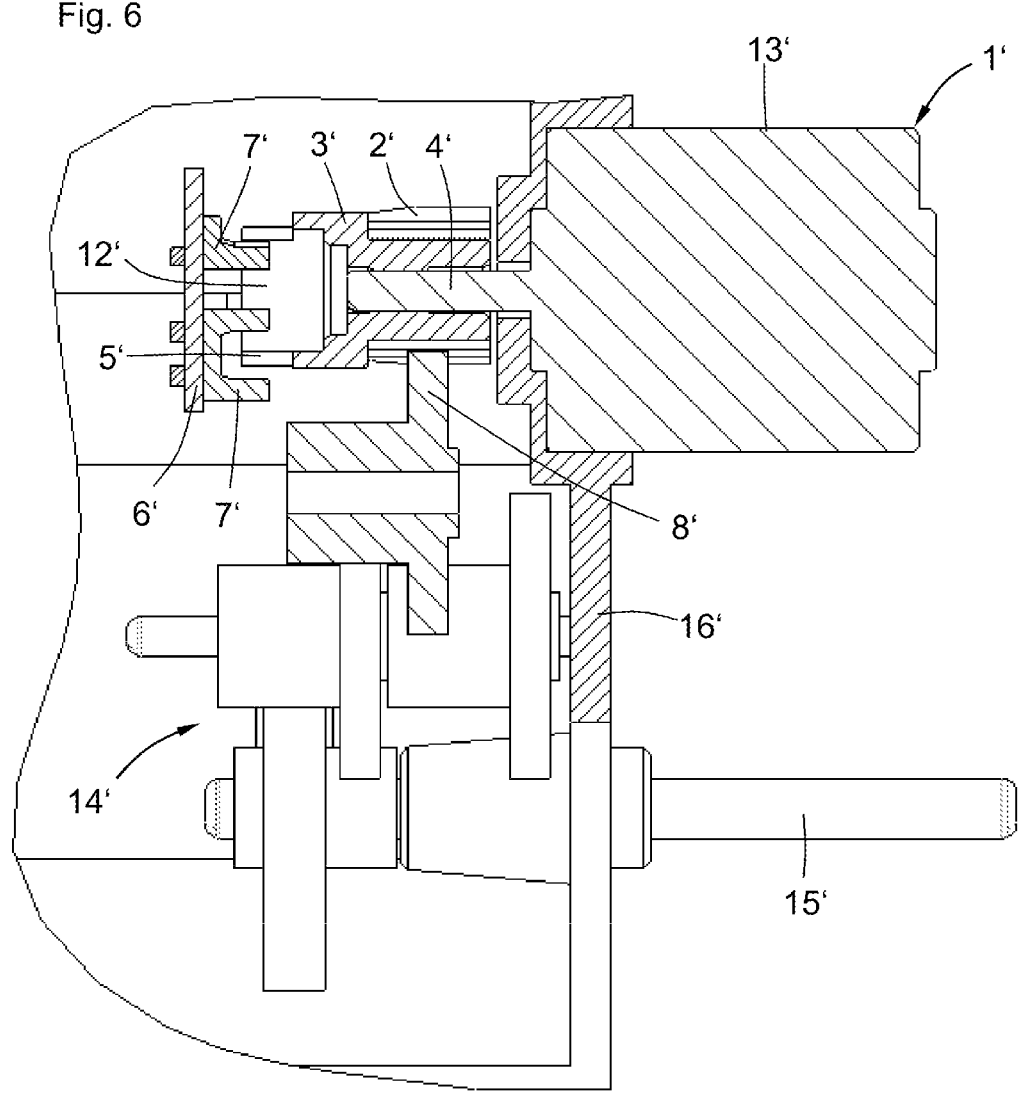
FIG. 6 is a cross-sectional view through a part of a syringe pump with the electric motor according to FIG. 4.

FIGS. 4 to 6 show a second exemplary embodiment of the invention, which differs from the first exemplary embodiment in the design of the sensor element 3'. The remaining components are essentially identical. Thus, in the second exemplary embodiment, the electric motor 1' also has a motor housing 13', through which a motor shaft 4' extends. The motor shaft 4' is connected in a way that precludes rotation to a motor pinion 2'. On the end face, the sensor element 3' adjoins the motor pinion 2'.

The sensor element 3' has a hollow-cylindrical design and has two material segments 12', which delimit two recesses 5'. The material segments 12' have a uniform wall thickness. Preferably, the material segments 12' have a uniform width so that the recesses 5' also have a uniform width. The recesses 5' are arranged radially opposite one another.

In contrast to the first exemplary embodiment, the second exemplary embodiment provides that the sensor element 3' has only two recesses 5'. These recesses 5' pass light beams from two rotary encoders 7', which are arranged on a common sensor circuit board 6'. The common sensor circuit board 6' is arranged axially spaced from the sensor element 3'.

The rotary encoders 7' each have a light-barrier element which is arranged radially inside the sensor element 3'. Each of the rotary encoders 7' also has a further light-emitting element which is arranged radially outside the sensor element 3'. The light beams 11 of the rotary encoders 7' are aligned at an acute angle to one another.

FIG. 6 shows, by means of the second exemplary embodiment, an arrangement of the electric motor 1 within a syringe pump. Such an arrangement can also be implemented in all further exemplary embodiments and is not restricted to the second exemplary embodiment.

In general, the injection pump has a drive housing 16', which accommodates the electric motor 1', in particular the motor housing 13'. A spur gear 14', which is coupled with the motor pinion 2' of the electric motor 1' via a spur gear 8', is also mounted in the drive housing 16'. The spur gear 14' acts on a threaded spindle 15'. The threaded spindle 15' is connected to a syringe piston receptacle. Thus, a movement of the threaded spindle 15' can be transmitted to a syringe plunger.

The syringe pump basically operates as follows. The motor shaft 4' is rotated by the electric motor 1'. The motor shaft 4' is connected in a way that precludes rotation to the motor pinion 2'. Thus the rotation of the motor shaft 4' is transmitted directly to the motor pinion 2', which consequently rotates at the same speed as the motor shaft 4'. The rotational speed and the direction of rotation are thereby determined by means of the rotary encoders 7' of the encoder and, if necessary, adjusted by means of preset values.

The motor pinion 2' meshes with the spur gear 8', the rotational movement of which is transmitted to the spur gear transmission 14'. The spur gear 14' transmits the rotary motion to the threaded spindle 15', which converts the rotary movement into a linear movement. By means of the transmission ratio of the spur gear 14', the thread spindle 15' performs a longitudinal-axial movement with a constant, specifically very slow, speed. For example, medications from a syringe can be dispensed continuously with constant fluid flow.

FIG. 7 shows a third exemplary embodiment of the invention. In essence, an electric motor 1" is shown including a motor shaft 4". A motor pinion 2" is connected in a way that precludes rotation to the motor shaft 4". A sensor element 3" protrudes beyond the motor shaft 4", which is designed in one piece with the motor pinion 2". The sensor element 3" comprises multiple recesses 5" which pass a light beam 11" of a rotary encoder 7". For this purpose, the rotary encoder 7" comprises a light source 9" and a light receiver 10" which are arranged radially opposite one another in relation to the motor shaft 4".

In the third exemplary embodiment according to FIG. 7, it is provided that the rotary encoder 7" is arranged completely radially outside the sensor element 3". In particular, the rotary encoder 7" has two light-emitting elements, in particular the light source 9" and the light receiver 10", which are each positioned radially outside the sensor element 2". The light beam 11" thus completely passes through the sensor element 3". For this purpose, it is provided that the sensor element 3" has at least two recesses 5" which are arranged radially opposite one another.

A fourth embodiment of the invention is shown in FIG. 8. An electric motor 1''' is shown, which has a motor housing 13'''. A motor shaft 4''' protrudes coaxially from the motor housing 13''', which is connected in a way that precludes rotation to a motor pinion 2'''. The motor pinion 2''' interlocks with a spur gear 8'''.

A sensor element 3''' adjoins the motor pinion 2''' longitudinally and integrally. The sensor element 3''' is essentially hollow-cylindrical in shape. In particular, the sensor element 3''' has one or more material segments 12''' which delimit at least one recess 5'''.

Arranged in the axial direction spaced from the motor housing 13''' is an encoder with a sensor circuit board 6''' and at least one rotary encoder 7''' which is firmly connected to the sensor circuit board 6'''. The rotary encoder 7''' includes a light source 9''' and a light receiver 10'''. The light source 9''' and the light receiver 10''' are arranged radially opposite each other. A light beam 11''' can be activated between the light source 9''' and the light receiver 10'''.

As it can be clearly seen in FIG. 8, the sensor element 3''' has a cross-sectional diameter that is markedly larger than the cross-sectional diameter of the motor pinion 2'''. Thus, even in the case of a small motor pinion 2''', a rotary encoder 7''' can be arranged in such a way that the light receiver 10''' is located radially inside the sensor element 3''', whereas the light source 9''' is located radially outside the sensor element 3'''. In particular, more than one rotary encoder 7''' may be provided in order to improve the accuracy of the measurement.

The above-described invention is generally suitable for particularly compact electric motors. Specifically, the invention is particularly suitable for electric motors with an outer diameter, specifically an outer diameter of the housing, of 8 mm.

It is to be understood that the present invention is not limited to the illustrated embodiments described herein. Various types and styles of user interfaces may be used in accordance with the present invention without limitation. Modifications and variations of the above-described embodiments of the present invention are possible, as appreciated by those skilled in the art in light of the above teachings. It is therefore to be understood that, within the scope of the appended claims and their equivalents, the invention may be practiced otherwise than as specifically described.

LIST OF REFERENCE SYMBOLS 1, 1', 1", 1''' Electric motor
2, 2', 2", 2''' Motor pinion
3, 3', 3", 3''' Sensor element
4, 4', 4", 4''' Motor shaft
5, 5', 5", 5''' Recess
6, 6', 6", 6''' Sensor circuit board
7, 7', 7", 7''' Rotary encoder
8, 8', 8", 8''' Spur gear
9", 9''' Light source
10", 10''' Light receiver
11", 11''' Light beam
12, 12', 12", 12''' Material segment
13, 13', 13", 13''' Motor housing
14' Spur gear motor
15' Threaded spindle
16' Drive housing

What is claimed is:

1. An electric motor comprising:
a motor housing;
a motor shaft extending out of the motor housing;
a motor pinion attached to the motor shaft;
an optical rotary encoder having a light beam from a light source and a light receiver;
a drum-shaped sensor element for use with the optical rotary encoder, the sensor element secured to the motor pinion and having at least one recess defined by at least two material segments for shadowing the light beam of the optical rotary encoder and for the transmission of the light beam from the optical rotary encoder to the light receiver, the motor pinion being arranged between the sensor element and the motor housing;
the sensor element being arranged between the light source and the light receiver in such a way that a direct light beam can be projected between the light source and the light receiver via the at least one recess and be shaded by the material segments; and
means for integrally forming the motor pinion and the sensing element with one another and being coupled with the motor shaft in a rotationally fixed manner, the sensor element extending axially beyond the motor shaft and being aligned coaxially with the motor pinion and the at least one recess being formed in the sensor element in such a way that the light beam of the rotary encoder can pass radially to the light receiver relative to a rotational axis of the sensor element wherein the light source and the light receiver are arranged radially outside the sensor element.

2. The electric motor according to claim 1, wherein the at least two material segments extend parallel to a rotational axis of the sensor element and define two recesses which are arranged radially opposite one another to provide a clear path completely through the sensor element so that the light beam can pass through the clear path to the light receiver.

3. The electric motor according to claim 2, wherein each of the at least two material segments has a cylindrical segment-shaped outer surface and a flat inner surface, the inner surfaces of the material segments being arranged parallel to each other and delimiting the clear path.

4. The electric motor according to claim 1, wherein the sensor element is a hollow cylindrical shape, and wherein the material segments have a uniform wall thickness and define at least two recesses.

5. The electric motor according to claim 4, wherein the number of recesses is three.

6. The electric motor according to claim 1, wherein the motor pinion and the sensor element are designed as a one-piece, injection-molded part.

7. The electric motor according to claim 1, wherein the light beam is aligned radially with respect to the longitudinal axis of the sensor element.

8. The electric motor according to claim 1, wherein the light source is radially arranged inside the sensor element, and the light receiver is radially arranged outside the sensor element.

9. The electric motor according to claim 1, wherein the light receiver is radially arranged inside the sensor element, and the light source is radially arranged outside the sensor element.

10. The electric motor according to claim 1 further comprising a sensor circuit board axially spaced from the sensor element and wherein the light source and the light receiver are mounted on the sensor circuit board.

11. The electric motor according to claim 1, further comprising at least two rotary encoders, each forming a light barrier; the light barriers being offset by an angle off the longitudinal axis of the sensor element which is not equal to 180 degrees.

12. The electric motor according to claim 1, further comprising at least two rotary encoders, each forming a light barrier; the light barriers being offset by an angle off the longitudinal axis of the sensor element which is not equal to 180 degrees.

13. A syringe pump or infusion pump with an electric motor according to claim 1.

* * * * *